United States Patent [19]

Lang

[11] Patent Number: 4,527,426
[45] Date of Patent: Jul. 9, 1985

[54] SYSTEM FOR CENTERING AN ELONGATED OBJECT WITHIN A HOUSING

[75] Inventor: John G. Lang, Scarborough, Canada
[73] Assignee: Rotesco Inc., Ontario, Canada
[21] Appl. No.: 499,541
[22] Filed: May 31, 1983
[51] Int. Cl.³ .............................................. G01L 5/04
[52] U.S. Cl. .................................. 73/158; 33/180 R
[58] Field of Search .......... 73/158; 33/180 R, 181 R, 33/172 D, 169 F; 254/389; 308/3.9, 4 R; 269/34, 243, 268; 403/43, 44, 45, 47

[56] References Cited

U.S. PATENT DOCUMENTS

| | | | |
|---|---|---|---|
| 311,716 | 2/1885 | Beecher et al. | 403/44 |
| 507,587 | 10/1893 | Lippitt | 269/243 |
| 1,954,920 | 4/1934 | Damerell | 269/34 |
| 2,336,980 | 12/1943 | Burke et al. | 73/158 |
| 3,769,714 | 12/1973 | Anderson | 33/180 R |

Primary Examiner—Charles Frankfort
Assistant Examiner—Patrick Scanlon

[57] ABSTRACT

The present invention provides an apparatus for centering an object within a housing. The apparatus comprises first and second spaced apart adjustable jaw arrangements aligned in the housing, an adjustment for adjusting the opening and closing of the jaw arrangements and first and second connecting members for connecting the first and second jaw arrangements respectively to the adjustment in a manner such that a single adjustment provides substantially simultaneous and corresponding adjustment of each of the first and second jaw arrangements.

13 Claims, 6 Drawing Figures

SYSTEM FOR CENTERING AN ELONGATED OBJECT WITHIN A HOUSING

FIELD OF THE INVENTION

The present invention relates to an apparatus for centering an object within a housing and is particularly useful for centering a wire rope within and passing through a magnetic testing head for testing the wire rope.

BACKGROUND OF THE INVENTION

There are many applications in which it is highly desirable to center an elongated object within a body fitted around the object. One specific example is found in wire rope testing devices which include a magnetic testing head through which the wire rope is passed. For purposes of maximizing testing results, the wire rope should be substantially centered within the test head. This centering can present problems particularly in view of the fact that wire ropes come in numerous different diameter sizes.

In the past the centering of different diameter sizes of wire ropes has been achieved by providing a plurality of sleeves of different thicknesses to be used with the magnetic testing head. According to this system a relatively thick wire rope is centered by using a thin sleeve whereas a relatively thin wire rope is centered using a thicker sleeve.

The problem encountered with this interchangeable sleeve centering method are two fold. Firstly the system necessitates the requirement for manufacturing many different thicknesses of sleeves for the many different sizes of wire ropes. Secondly the multi-sleeve system substantially reduces the portability of the test head simply from the fact that the person testing these wire ropes must at the same time be carrying a plurality of testing sleeves which are both bulky and relatively heavy. Both the bulk and the weight are substantial problems in that much of the wire rope testing is done directly in the field.

SUMMARY OF THE PRESENT INVENTION

The present invention provides apparatus for centering an object within a housing and has particular application for use in wire rope testing heads. Specifically the apparatus of the present invention comprises first and second spaced apart adjustable jaw arrangements aligned in the housing, adjustment means for adjusting opening and closing of the jaw arrangements and first and second connecting means for connecting the first and second jaw arrangements respectively to the adjustment means in a manner such that a single adjustment of the adjustment means provides substantially simultaneous and corresponding adjustment of each of the first and second jaw arrangements.

The centering system according to the present invention when used in a wire rope testing device makes it possible to quickly and easily center essentially any size wire rope without requiring numerous replacement parts within the testing device. This substantially reduces both the complexity and the bulk of the testing device.

According to an aspect of the present invention the adjustable jaw arrangement or assembly and the adjustment means for opening and closing the jaw assembly comprises a first jaw member connected directly with the adjustment means and a second jaw member detached from the first jaw member and controlled by the first jaw member in a manner such that the two jaw members when adjusted move in opposing directions to open and close about the object substantially in unison with one another.

BRIEF DISCUSSION OF THE DRAWINGS

The above as well as other advantages and features of the present invention will be described in greater detail according to the preferred embodiments of the present invention in which.

DETAILED DESCRIPTION ACCORDING TO THE PREFERRED EMBODIMENTS

Figure 1:
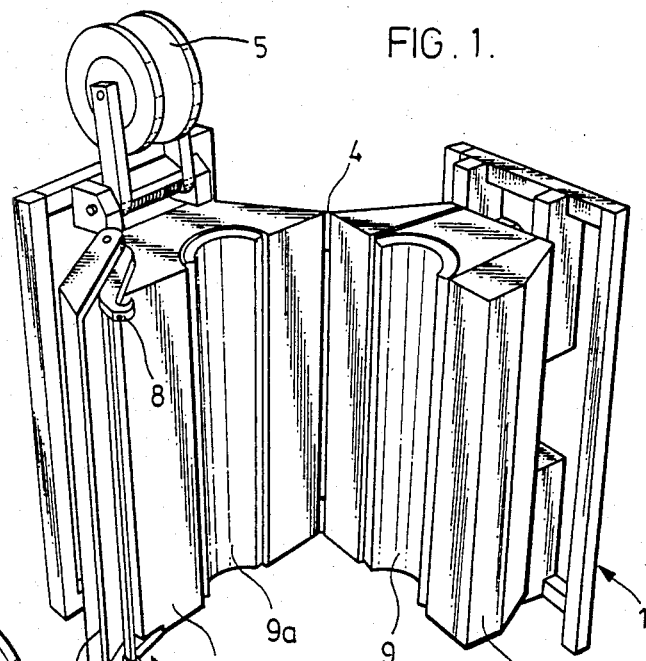
FIG. 1 is a perspective view of a preferred embodiment test head in an open position.
Figure 2:
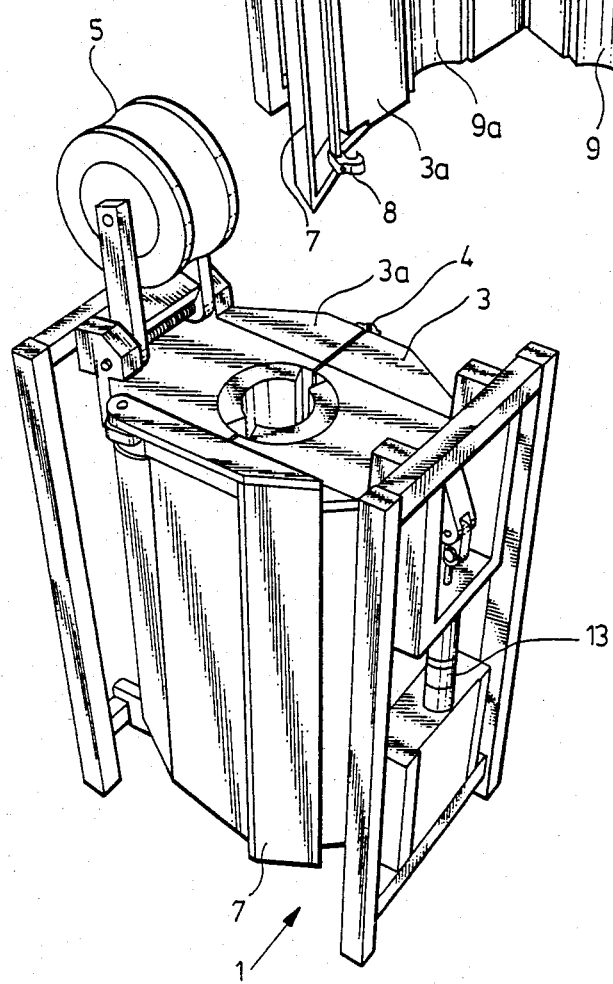
FIG. 2 is a perspective view of the test head shown in FIG. 1 when in a closed position.

FIGS. 1 and 2 show a test head generally indicated at 1 which is used in the magnetic testing of wire ropes. This particular test head comprises a pair of body portions 3 and 3a hinged at 4 to open and close for receiving a wire rope to be passed through the test head. The test head further includes a guide wheel 5 which rotates over the wire rope as it travels through the test head. Also provided is a closure reverse action lever clamp mechanism comprising a clamp 7 having hook portions 8 for clamping the unit closed in the FIG. 2 position.

Figure 3:
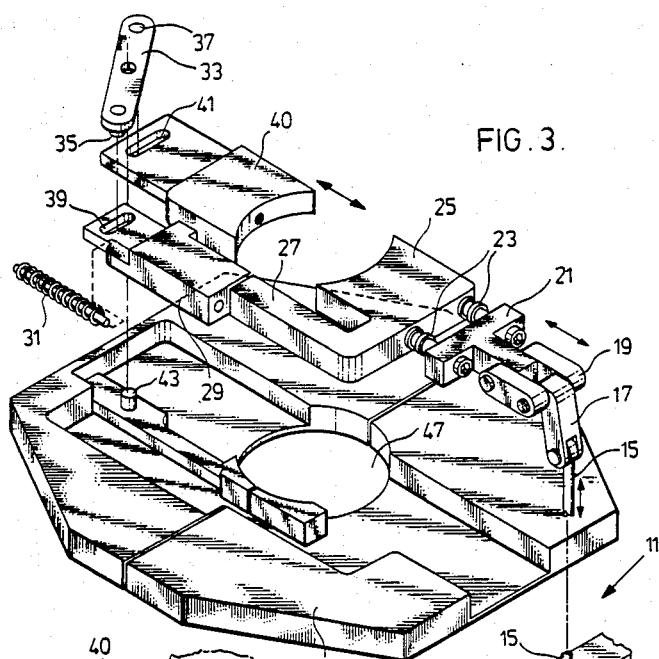
FIG. 3 is an exploded perspective view of an adjustment means and a jaw assembly being used in the test head of FIGS. 1 and 2 according to a preferred embodiment of the present invention.

FIG. 3 shows an adjustment and jaw assembly which is used for the centering of various different sizes of wire ropes within the test head of FIGS. 1 and 2. The reason for the requirement of a centering system is that the test head includes magnetic flux sensors spaced around the test head and in order to achieve the most meaningful test results the wire rope should be centered so that it is located in a central position relative to all of the sensors. This position is substantially at the center of the test head which includes a pair of sleeve portions 9 and 9a best shown in FIG. 4 for moving the wire rope to the central position. However, it should be understood that there are many different diameter sizes for wire rope so that the positions of sleeve portions 9 and 9a will vary in accordance with the wire rope diameter. The centering system of the present invention is one which provides automatic positioning for the centering of a wire rope within the test head regardless of the wire rope diameter. Furthermore and in contrast to prior art systems, this is done without requiring the replacement of the sleeve portions with sleeve portions of various different thicknesses.

Referring more specifically to FIG. 3 the jaw assembly itself comprises a pair of opposing jaws 25 and 40 which are fitted to the outside of sleeve portions 9 and 9a respectively. These two jaw portions although moveable in combination with one another are not attached which allows the opening of the test head as shown in FIG. 1.

Jaw portion 25 is connected through a link connecting assembly to a turnbuckle-like adjustment member 13 which extends longitudinally along the side of the test head at substantially 90 degrees to the jaw assembly. It should be noted that although only one upper jaw assembly is shown in FIG. 3, a substantially identical jaw assembly is also provided at the opposite lower end of the test head. A single adjustment of turnbuckle 13 simultaneously controls adjustment of both of these jaw assemblies.

Threaded into turnbuckle 13 are a pair of threaded connecting members 15 extending to the upper and lower ends of the test head. Each of the threaded connecting members is connected to the link system referred to above and comprising a first link member 17 and a second link member 19 which is at substantially 90 degrees to the threaded connecting member. Link 17 is pivotal with respect to both the threaded connecting member and link 19 for converting the longitudinal positioning of the threaded connecting members to a transverse adjustment of the jaw assembly.

Link 19 is on the other hand supported in a non-pivoting position to a T-shaped support member 21. This support member is provided with a pair of spring loaded arms 23 to which jaw member 25 is mounted in a manner which allows forced positional adjustments of the jaw member as will be described later in detail.

Also provided in the jaw assembly is a movement transfer plate 29 as well as a pivotal member 33. These components as well as the two jaw members are mounted within a plate 45 recessed as shown in FIG. 3 to receive and guide movement of the overall jaw assembly. This plate is further provided with a central opening 47 which when the jaw assembly is fitted in the test head provides a seat for the two sleeve portions. As it is to be appreciated this entire arrangement is duplicated at the opposite end of the test head.

The centering of the two sleeve portions is accomplished as follows. Turnbuckle adjustment 13 is rotated in a direction to either cause opening or closing of the two jaw members at each jaw assembly. Adjustment member 13 has a central threaded bore into which the two connecting members are threadably received with the threads on the connecting members being turned in a direction such that the two connecting members automatically move in opposite directions to one another with a single adjustment of the turnbuckle system, i.e. the two connecting members either move simultaneously inwardly or outwardly relative to the adjustment member. An outward pushing on the connecting members through the adjustment member causes closing of the upper and lower clamping jaws whereas an inwardly pulling or drawing of the two connecting members by a single threaded adjustment of the adjustment member causes simultaneous opening of the two jaw assemblies.

Figure 5:
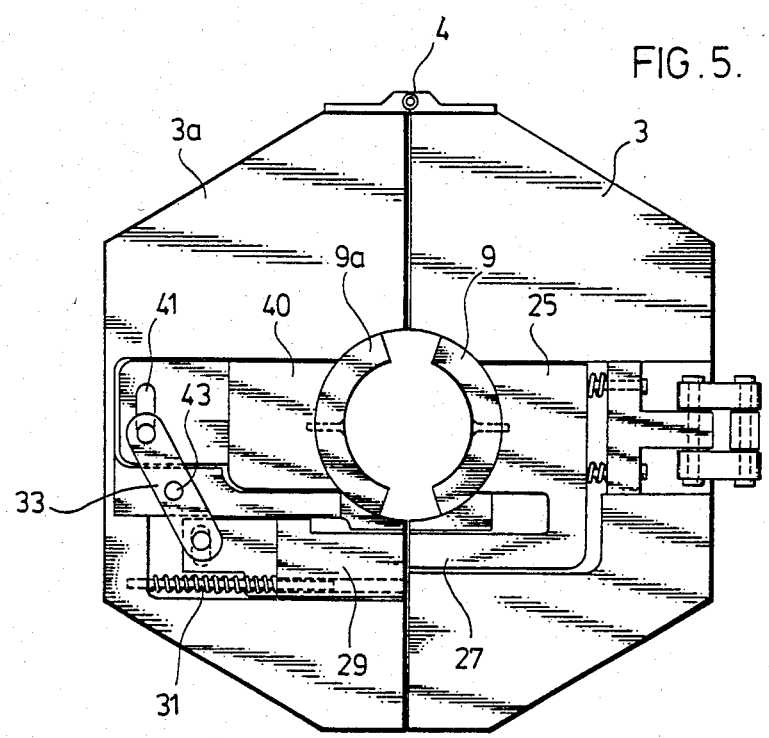
FIGS. 5 and 6 are bottom plan views of the test head.
Figure 6:
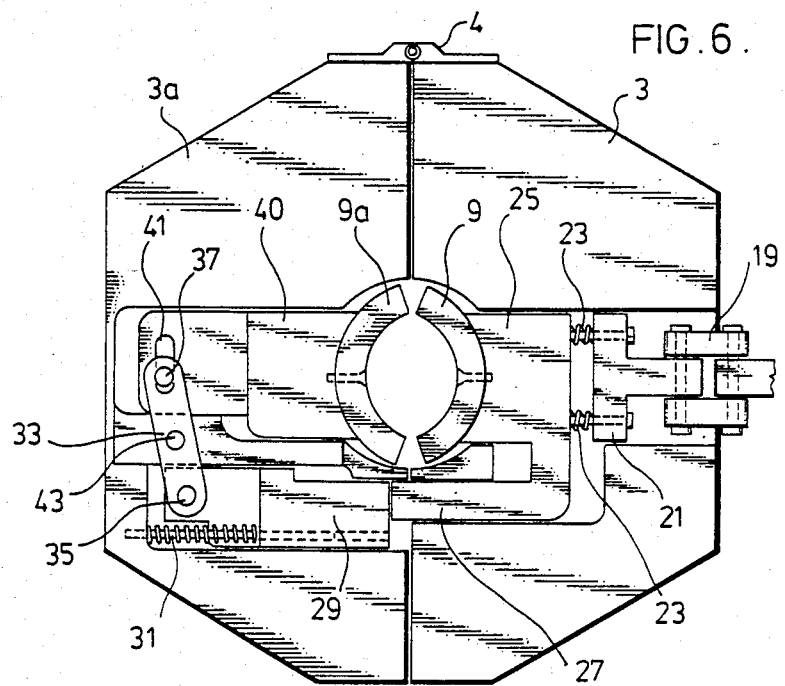

In a situation where the two connecting members are pushed outwardly by a single adjustment of the threaded adjustment member this outward movement is transferred through the link assembly to a inward pushing action on jaw member 25 through the spring loaded arm 23 of T-shaped support member 21. The inward transverse movement of jaw 25 is guided by means of the channeling action in plate 45. Jaw member 25 is provided with a projecting arm 27 which is in direct contact with movement transfer member 29 which is slideably mounted to slide within plate 45. The movement transfer member is as best shown in FIGS. 5 and 6, biased by a spring and rod combination 31 to maintain constant contact with the arm 27 of jaw member 25. The pivot member 33 is provided with a pin 35 which fits into groove 39 at the far end of the movement transfer member for connecting the movement transfer member with the pivot member. The pivot member itself is mounted to plate 45 by means of a pivot pin 43 which fits into a centrally positioned aperture on the pivot member. The pivot member is provided with a further pin 37 at its opposite end from pin 35 which is received in a groove 41 at the outward end of jaw 40 thus completing the chain of contacts from the first to the second jaw member.

As the first jaw member is being closed arm 27 pushes on the movement transfer member 39 which slides in the same direction as the first jaw member. The movement transfer member in turn pushes on the pin 35 end of the pivot member causing pivot member 33 to pivot about pin 43 and to push inwardly on jaw 40 to move in the opposite direction to jaw 25 Therefore the closing action on jaw 25 is transferred to jaw 40 which closes simultaneously with jaw 25. Furthermore as a result of the central pivoting of pivot member 33 the two jaws close by substantially equal amounts with a single adjustment of threaded adjustment member 13.

For purposes of opening the two jaw members the turnbuckle adjustment system is simply rotated in the opposite direction to that described above thus causing a retracting or opening movement on jaw 25. As mentioned above, movement transfer member 29 is spring loaded to maintain constant contact with arm 27 of jaw member 25 so that the movement transfer member provides an inward pulling action on pin 35 of pivot member 33 as jaw member 25 is opened. The pivoting action of the pivot member causes an outward pushing action by pin 37 on jaw 40 to cause the second or free jaw to move outwardly simultaneously with and by the same amount as jaw 25 which is connected directly to the threaded adjustment system.

Figure 4:
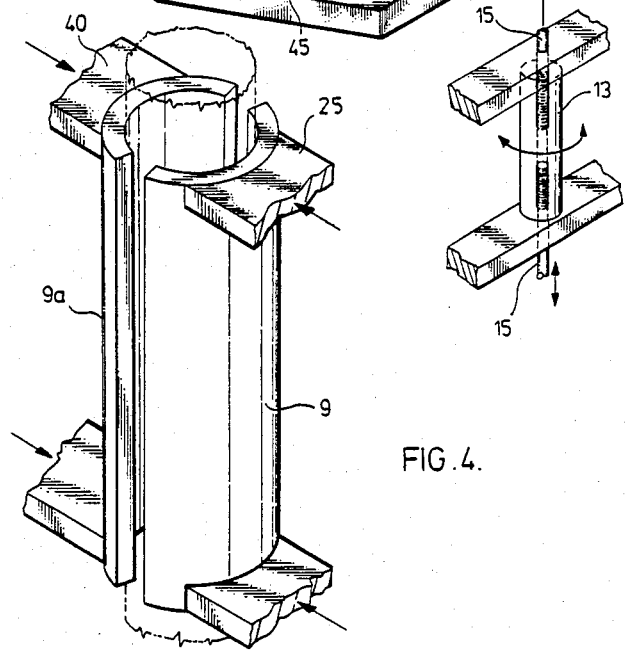
FIG. 4 is a perspective view of the sleeve region of the test head of FIGS. 1 and 2.

As can be seen in FIG. 4, 5 and 6, sleeve portions 9 and 9a are secured directly to the two jaw members so that they move with the opening and closing of each of the jaw assemblies. FIG. 5 shows the two sleeve portions in a spread position for receiving a relatively large diameter wire rope whereas FIG. 6 shows the sleeve portions in a much closer set position for receiving a relatively small diameter wire rope. As will be seen in these two figures the centering system of the present invention provides an adjustment whereby the two sleeve portions are located at substantially identical positions in the opposite halves of the test head. It would also be appreciated from FIGS. 5 and 6 that when the test head is opened for receiving the wire rope the jaw assembly will separate at the interface between arm 27 of jaw 25 and movement transfer member 29.

The springy connection 23 of jaw member 25 to support member 21 provides a means for allowing the two jaw members and the attached sleeve portions to automatically open and then spring back to the appropriate position should some sort of an obstruction be found on the wire rope which increases its outside diameter at a single location along the wire. For example, should there be a protrusion at the outside of the wire rope, the protrusion will cause a forced opening of the two sleeve portions to allow the protrusion to pass through the test head. This opening is permitted as a result of the slideable spring loaded mounting of the first jaw on the support arms 23 which allow springed opening of the sleeve portions without affecting the actual adjusted position of the two jaw members. After the protrusion has passed through the test head the springs at connection 23 which are compressed during the opening of the two jaw members spring back to their normal position causing the first jaw member 25 to return to its adjusted position with the first jaw member acting on the second member to automatically return to its adjusted position as well.

As will be seen from the above, the centering system for the present invention provides for the centering of many different sizes of wire ropes within the test head without the need for numerous different interchangeable sleeves. Furthermore a single adjustment causes simultaneous and equal adjustment at not only both ends but also at both sides of the centering system provided within the test head.

It is to be understood that the centering system described can be used in numerous other applications where it is desirable to center an object within a housing. Therefore, although various preferred embodiments of the present invention have been described herein in detail it will be appreciated by those skilled in the art that variations may be made thereto without departing from the spirit of the invention or the scope of the appended claims.

The embodiments of the invention in which an exclusive property or privilege is claimed are defined as follows:

1. Apparatus for centering an object within a housing, said apparatus comprising first and second spaced apart adjustable jaw arrangements aligned in the housing, adjustment means for adjusting opening and closing of said jaw arrangements each of which comprises first and second jaw members located to either side of the object, said first jaw member being interconnected with said adjustment means and said second jaw member being separate from said first jaw member in each jaw arrangement and movement transfer means including a pivotal member in each jaw arrangement for transferring movement from said first jaw member to said second jaw member in a manner such that said jaw members move in opposing directions to open and close substantially simultaneously with one another, spring means for pressurizing said movement transfer means for maintaining contact between said movement transfer means and said first jaw member during opening thereof to provide automatic opening of said second jaw member during adjusted opening of said first jaw member, and first and second connecting means for connecting said first and second jaw arrangements respectively to said adjustment means such that a single adjustment of said adjustment means provides substantially simultaneous and corresponding adjustment of each of said first and second jaw arrangements, said first and second connecting means being threadably engaged with said adjustment means through opposite ends thereof to form a turnbuckle structure for threaded adjustment of said jaw arrangements.

2. Apparatus as claimed in claim 1, wherein said pivot member has a first end mounted to a movement transfer member for transferring movement from said first jaw member through said pivot member to said second jaw member and a second end mounted to said second jaw member with said pivotal member being pivotally mounted to said apparatus between said first and second ends thereof such that said movement transfer member and said second jaw member move in opposing directions with said spring means biasing said movement transfer member to a position for transferring movement from said first jaw member to said second jaw member whereby adjustment of said first jaw member in a first direction causes movement of said movement transfer member in such first direction and provides adjustment of said second jaw member in second direction opposite to such first direction for substantially simultaneous opening and closing of said first and second jaw members.

3. Apparatus as claimed in claim 2, including an arm from said first jaw member to said movement transfer member which is slideable within a movement guiding channel for transferring movement from said arm of said first jaw member to said second jaw member through said pivot member.

4. Apparatus as claimed in claim 3, including a plate in which said movement guiding channel is provided, said plate being further provided with adjustment guide channels for guiding adjustment of said first and second jaw members.

5. A wire rope testing device provided with centering means for centering a wire rope guide in said device, said centering means comprising first and second spaced apart jaw assemblies aligned in said testing device and each of said jaw assemblies comprising first and second jaw members to opposite sides of the wire rope guide, said first and second jaw members being detached from one another and being adapted to move substantially in unison for corresponding opening and closing of each jaw member relative to the wire rope guide, a turnbuckle adjustment for adjusting opening and closing of said jaw assemblies, said first jaw member of each assembly being connected to said adjustment member and including a movement transfer arrangement for transfering movement from said first jaw member to said second jaw member, said movement transfer arrangement comprising a sliding member which is biased by spring means to move with said first jaw member and a pivotal member pivotally connecting said second jaw member to said sliding member in a manner such that movement of said first jaw member in a first direction is transferred to move said second jaw member in a second direction, opposite to said first direction for substantially simultaneous opening and closing of said jaw members with a single adjustment of said adjustment member, said turnbuckle adjustment arrangement comprising a threaded adjustment member and first and second threaded connecting members for connecting said first and second jaw assemblies respectively to said adjustment member.

6. A wire rope testing device as claimed in claim 5, including a spring attachment of said first jaw member to said adjustment arrangement, said spring attachment allowing forced opening of each jaw assembly from a preset position and automatic closing back to the preset position following such forced opening.

7. A wire rope testing device as claimed in claim 5, wherein said turnbuckle adjustment arrangement extends longitudinally of said device and said jaw assemblies extend at substantially right angles thereto and wherein each of said connecting members includes pivotal linking means for inward and outward movement of said jaw assemblies with extension and retraction of said connecting means through the adjustment of said adjustment member.

8. A wire rope testing device as claimed in claim 5, wherein said device comprises first and second housing sections hingedly connected to one another for opening and closing of said device to fit a wire rope therein, said sliding member being separable from said first jaw member such that said housing sections open therebetween, and including spring means for biasing said sliding member into contact with said first jaw member when said housing sections are closed.

9. A wire rope testing device as claimed in claim 8, including a reverse action levered clamp for opening and closing said housing sections.

10. Apparatus for centering an object within a housing, said apparatus comprising an adjustable jaw assembly and adjustment means for adjusting opening and closing of said jaw assembly, said jaw assembly comprising a first jaw member connected directly with said adjustment means and a second jaw member detached from said first jaw member and controlled by said first jaw member in a manner such that said jaw members, when adjusted, move in opposing directions to open and close about the object substantially in unison with one another, said jaw assembly including a movement transfer mechanism including a pusher member for transferring and reversing direction of movement from said first jaw member to said second jaw member, said first and second jaw members being separable from one another at said pusher member, said housing comprising first and second housing sections which are adapted to open and close for fitting of the object therein, said first jaw member being located in said first housing section and said second jaw member being located in said second housing section such that said first and second jaw member separate from one another as said housing is opened, and including spring means for biasing said pusher member to a connecting position for interconnecting said first and second jaw members through said pusher member when said housing is closed.

11. Apparatus as claimed in claim 10 wherein said movement transfer mechanism is located in said second housing section with said second jaw member and wherein said pusher member separates from said first jaw member with opening of said housing.

12. Apparatus as claimed in claim 11 wherein said pusher member is slideable for sliding with adjustment of said first jaw member and including a pivotal member connecting said pusher member with said second jaw member and for reversing the direction of movement from said first jaw member to said second jaw member such that said jaw members simultaneously open and close with one another.

13. Apparatus as claimed in claims 10, 11 or 12, including a spring connection between said first jaw member and said adjustment means for forced opening of said jaw members from a preset position and automatic return of said jaw members to such preset position.

* * * * *